(12) United States Patent
Rozen et al.

(10) Patent No.: US 11,806,237 B2
(45) Date of Patent: Nov. 7, 2023

(54) METHODS AND SYSTEMS FOR ANNULOPLASTY ALIGNMENT

(71) Applicant: VALCARE, INC., Herzelyia Pituach (IL)

(72) Inventors: Yoav Rozen, Binyamina (IL); Nadav Yellin, Even Yehuda (IL); Shuki Porath, Haifa (IL); Yuri Falkovich, Pardes Hana (IL)

(73) Assignee: VALCARE, INC., Herzelyia Pituach (IL)

( * ) Notice: Subject to any disclaimer, the term of this patent is extended or adjusted under 35 U.S.C. 154(b) by 0 days.

(21) Appl. No.: 18/245,288

(22) PCT Filed: Sep. 15, 2021

(86) PCT No.: PCT/US2021/071467
§ 371 (c)(1),
(2) Date: Mar. 14, 2023

(87) PCT Pub. No.: WO2022/061344
PCT Pub. Date: Mar. 24, 2022

(65) Prior Publication Data
US 2023/0255772 A1    Aug. 17, 2023

Related U.S. Application Data

(60) Provisional application No. 63/078,770, filed on Sep. 15, 2020.

(51) Int. Cl.
*A61F 2/24* (2006.01)

(52) U.S. Cl.
CPC .......... *A61F 2/2466* (2013.01); *A61F 2/2448* (2013.01)

(58) Field of Classification Search
CPC .... A61F 2/2442; A61F 2/2445; A61F 2/2448; A61F 2/2466
See application file for complete search history.

(56) References Cited

U.S. PATENT DOCUMENTS

| | | |
|---|---|---|
| 2008/0262609 A1 | 10/2008 | Gross et al. |
| 2013/0226289 A1 | 8/2013 | Shaolian et al. |
| 2015/0112432 A1* | 4/2015 | Reich .................... A61F 2/2445 623/2.37 |
| 2015/0127093 A1 | 5/2015 | Hosmer et al. |

OTHER PUBLICATIONS

PCT/US2021/071467, International Search Report and Written Opinion, dated Jan. 14, 2022, 12 pages.

* cited by examiner

*Primary Examiner* — William H Matthews
(74) *Attorney, Agent, or Firm* — Dorsey & Whitney LLP (57) ABSTRACT

The present disclosure relates to methods, systems, subsystems, and kits for aligning an annuloplasty ring or a toroidal portion thereof with a natural fiducial in an annular target.

22 Claims, 7 Drawing Sheets

METHODS AND SYSTEMS FOR ANNULOPLASTY ALIGNMENT

RELATED CASES

This application is a 35 U.S.C. 371 National Phase application claiming priority to PCT/US2021/071467, filed Sep. 15, 2021, which claims priority to U.S. Provisional Application No. 63/078,770, filed on Sep. 15, 2020, and titled "METHODS AND SYSTEMS FOR ANNULOPLASTY ALIGNMENT," both of which are hereby incorporated by reference in their entirety.

BACKGROUND

The present disclosure is directed to methods and systems for aligning annuloplasty rings during surgical procedures. Specifically, the disclosure is directed to methods and systems for aligning annuloplasty ring or a toroidal portion thereof with natural fiducials present at, or near an annular target.

Annuloplasty remains a fundamental component in heart-valve repair. The annuloplasty ring may be used to restore the size and shape of the native annulus; to prevent future annular dilatation; and to provide functional annular support.

For example, dilation of the annulus of the mitral valve (MV) prevents the valve leaflets from fully coapting when the valve is closed, leading to mitral regurgitation (MR) of blood from the left ventricle into the left atrium.

Under typical circumstances, in MV repair, ring annuloplasty, once finished and anchored to the annulus, drastically reduces the mobility of the central posterior leaflet, causing valve closure to be a single anterior leaflet process with a frozen posterior buttress. Accordingly, and to ensure full coaptation of the leaflets, it is advantageous to properly locate the annuloplasty ring within the annulus.

Similarly, tricuspid regurgitation (TR) of the tricuspid valve (TV) is thought to affect a majority of the population in the U.S. Regardless, relatively few TV operations are performed annually due to various challenges associated with surgical or percutaneous transcatheter based treatment of TR.

For example, since the TV annulus is relatively large (at least compared to the MV), not calcific, and has a dynamic 3D structure (e.g., during the cardiac cycle), the ability to get proper anchoring of the annuloplasty ring becomes challenging. Moreover, the sensitivity resulting from proximity of conduction systems, such as the bundle of His, which is a direct continuation of the atrioventricular (AV) node, lies in the muscular portion of the atrioventricular septum, near the ostium of the coronary sinus (at the apex of the triangle of Koch) and passes through the right trigon of the central fibrous body to reach the ventricular septum, thus making proper ring alignment during annuloplasty a major consideration.

The proposed technology aims to address the shortcomings of the current systems.

SUMMARY

In an exemplary implementation, provided herein is a method of aligning an annuloplasty ring with at least one natural fiducial in an annular target, implementable in a system comprising: an annuloplasty ring having an outer hollow tube, or a toroidal portion thereof, with a plurality of segments, operable to change the outer hollow tube from an insertion configuration to an operable configuration; an alignment member, releasably coupled to the outer hollow tube via at least one coupling assembly, the at least one coupling assembly configured to be aligned with the at least one natural fiducial; and a delivery catheter adapted, sized, and configured to accommodate: the alignment member and the annuloplasty ring in its insertion configuration, wherein the delivery catheter is operable, once the annuloplasty ring is inserted, to alter the outer hollow tube from the insertion configuration to the operable configuration, the method comprising: using the delivery catheter, introducing the annuloplasty ring or its toroidal portion to the annular target; using the delivery catheter, altering the insertion configuration of the annuloplasty ring or its toroidal portion to the operable configuration; and using the alignment member, aligning the at least one coupling assembly with the at least one natural fiducial, thereby aligning the annuloplasty ring or its toroidal portion with the at least one natural fiducial in the annular target.

In another exemplary implementation, provided herein is a method of aligning an annuloplasty ring, or a toroidal portion thereof, with at least one natural fiducial in an annular target, implementable in a system comprising: an annuloplasty ring or a toroidal portion thereof, each having an outer hollow tube with a plurality of segments, operable to change the outer hollow tube from an insertion configuration to an operable configuration; an alignment member comprising a pair of stylets, each stylet having a distal eyelet, releasably coupled to the outer hollow tube via at least two coupling assemblies, wherein each coupling assembly is coupled to the alignment member via each eyelet and is configured to be aligned with the at least one natural fiducial; and a delivery catheter adapted, sized, and configured to accommodate: the alignment member and the annuloplasty ring or its toroidal portion in its insertion configuration, and wherein the delivery catheter is operable, once the annuloplasty ring is inserted, to alter the outer hollow tube from the insertion configuration to the operable configuration, the method comprising: using the delivery catheter, introducing the annuloplasty ring or its toroidal portion to the annular target; using the delivery catheter, altering the elongated insertion configuration of the annuloplasty ring to the operable annular configuration; and using the alignment members, aligning at least one of the pair of coupling assembly with the at least one natural fiducial.

In yet another exemplary implementation, the annuloplasty ring or its toroidal portion each has one or more zones, each zone comprising a plurality of internal anchor members located at least partially within the outer hollow tube, each anchor operable to selectably extend radially from the outer hollow tube and engage a portion of the annular target, wherein the method further comprises: using the plurality of anchoring members, anchoring the annuloplasty ring or its toroidal portion to a predetermined portion of the annular target; and using the delivery catheter, releasing the alignment member, thereby aligning the annuloplasty ring with the at least one natural fiducial in the annular target.

In an exemplary implementation, provided is the use of a system comprising: an annuloplasty ring having an outer hollow tube, or a toroidal portion thereof, with a plurality of segments, operable to change the outer hollow tube from an insertion configuration to an operable configuration; an alignment member, releasably coupled to the outer hollow tube via at least one coupling assembly, the at least one coupling assembly configured to be aligned with the at least one natural fiducial; and a delivery catheter adapted, sized, and configured to accommodate: the alignment member and the annuloplasty ring in its insertion configuration, wherein the delivery catheter is operable, once the annuloplasty ring is inserted, to alter the outer hollow tube from the insertion configuration to the operable configuration, in the process of aligning an annuloplasty ring or a toroidal portion thereof with at least one natural fiducial in an annular target, by performing the steps of: using the delivery catheter, introducing the annuloplasty ring, or its toroidal portion to the annular target; using the delivery catheter, altering the insertion configuration of the annuloplasty ring to the operable configuration; and using the alignment member, aligning the at least one coupling assembly with the at least one natural fiducial, thereby aligning the annuloplasty ring, or its toroidal portion with the at least one natural fiducial in the annular target.

BRIEF DESCRIPTION OF THE DRAWINGS

The steps of the method implementable using the alignment systems disclosed herein will become apparent from the following detailed description when read in conjunction with the figures, which are exemplary, not limiting, and in which.

While the disclosure of the methods implementable using the alignment systems disclosed herein is amenable to various modifications and alternative forms, specifics thereof have been shown by way of example in the drawings and will be further described in detail hereinbelow. It should be understood, however, that the intention is not to limit the disclosure to the particular exemplary implementations described. On the contrary, the intention is to cover all modifications, equivalents, and alternatives.

DETAILED DESCRIPTION

Provided herein are exemplary implementations of a methods, systems, subsystems and kits for aligning an annuloplasty ring, or a toroidal portion thereof, with a natural fiducial in an annular target. The annular target can be, for example a pulmonary valve, a mitral valve, a tricuspid valve, or an aortic valve.

Furthermore, and as is typically the case, the three dimensional profile of the annulus in some of these valves is dynamic during the cardiac cycle absent implantation of the annuloplasty ring or its toroidal portion, making proper alignment using the methods and systems disclosed beneficial for proper operation of the valves. Furthermore, in the context of the disclosure, the term annuloplasty ring, or its toroidal portion, does not necessarily mean a ring defining a single plane, but rather encompasses other planes, for example a saddle-shaped ring.

Likewise, the term "its toroidal portion" means, in the context of the disclosure, any part of the ring operable to be adjoined to form the full annuloplasty ring. For example, in certain implementations, the toroidal portion can be less than half the full ring, or less than quarter of the full ring and be operable to adjoin other components and form the full annuloplasty ring.

Definitions

The term "coupled", including its various forms such as "operably coupling", "coupling" or "couplable", refers to and comprises any direct or indirect structural coupling, connection, or attachment or adaptation or capability for such a direct or indirect structural or operational coupling, connection, or attachment, including integrally formed components and components which are coupled via or through another component or by the forming process. Indirect coupling may involve coupling through an intermediary member or adhesive, or abutting and otherwise resting against, whether frictionally or by separate means without any physical connection.

In addition, for the purposes of the present disclosure, directional or positional terms such as "top", "bottom", "upper", "lower", "side", "front", "frontal", "forward", "rear", "rearward", "back", "trailing", "above", "below", "left", "right", "radial", "vertical", "upward", "downward", "outer", "inner", "exterior", "interior", "intermediate", "apical", "basal", etc., are merely used for convenience in describing the various exemplary implementations of the present disclosure.

Likewise, the term "engage" and various forms thereof, when used with reference to an engaging element, for example in the engagement of fin 310 between the pair of release cords 305, 305', refers in an exemplary implementation to the application of any forces that tend to hold fin 310 and the pair of release cords 305, 305' together against inadvertent or undesired separating forces (e.g., such as may be introduced during alignment of the annuloplasty ring or its toroidal portion). It is to be understood, however, that engagement does not in all cases require an interlocking connection that is maintained against every conceivable type or magnitude of separating force. Further, the term "engaging element" refers in another exemplary implementation to one or a plurality of coupled components, at least one of which is configured for releasably engaging another element. Thus, this term encompasses both single part engaging elements and multi-part-assemblies, for example coupling assembly 303 as a whole.

The terms "first", "second", and the like, herein do not denote any order, quantity, or importance, but rather are used to denote one element from another. The terms "a", "an", and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., stylet(s) 302, 302' includes one or more stylet). Reference throughout the specification to "one exemplary implementation", "another exemplary implementation", "an exemplary implementation", and so forth, means that a particular element (e.g., step, feature, structure, and/or characteristic) described in connection with the exemplary implementation is included in at least one exemplary implementation described herein, and may or may not be present in other exemplary implementations. In addition, it is to be understood that the described elements may be combined in any suitable manner in the various exemplary implementations.

In the context of the disclosure, the term "operable" means the system and/or the device, or a certain element or step is fully functional, sized, adapted and calibrated, comprises elements for, and meets applicable operability requirements to perform a recited function when activated, coupled, implemented, actuated, effected, or realized. In relation to systems, the term "operable" means the system is fully functional and calibrated, having the necessary elements, as well as the mechanisms for, and meets applicable operability requirements to perform a recited function when executed by a user.

The term "abut" refers in the context of the disclosure, to items that are in direct physical contact with each other, although the items may not be attached, secured, fused, glued, sewn, or welded together.

In the context of the disclosure, the term "natural fiducial" is used to describe an identifiably distinctive anatomical feature including, without limitation, right fibrous trigon, left fibrous trigon, interleaflet triangle, tricuspid posterior-anterior hinge, or a combination comprising one or more of the foregoing.

In the context of the disclosure, the term "aligned" is a broad term and is generally meant to include, without limitation, having a fixed angular relationship between about 0 degrees and about 180 degrees between at least one coupling assembly, the delivery catheter, or a marker on the annuloplasty ring or its toroidal portion, and at least on natural fiducial.

In the context of the disclosure, the term "hairpin-shaped" is not intended to be limited to U-shaped conductors, and instead refers generally to a distinct wire segment having two ends, whether or not a U-shaped portion is included between the two ends.

In the context of the disclosure, the term "stylet" refers to any inner component of a device such as the delivery catheter, and specifically including a "wire", with a proximal end, a distal end, and with a functional tip that is designed to perform or assist in a designated procedure. To be more precise, stylet is defined as a flexible device which fits within a delivery catheter and may be passed there-through. In other words, the stylet disclosed involves a flexible device having an eyelet located at a distal end thereof. The stylet is resilient and is so constructed that it bends easily but can be pushed along its length.

In the context of the disclosure, the term "saddle-shaped" is used herein to mean an annuloplasty ring generally made of two arcuate members, for example, two toroidal portions with each toroidal portion having an apex and two ends connecting the toroidal portions. The apex of the toroidal portion in one member can be in the same or opposite direction of the other member. The formed ring can be generally D-shaped.

A more complete understanding of the methods, systems, subsystems, and kits for aligning an annuloplasty ring, or a toroidal portion thereof with a natural fiducial in an annular target, can be obtained by reference to the accompanying drawings. These figures (also referred to herein as "FIG(S).") are merely schematic representations based on convenience and the ease of demonstrating the present disclosure, and are, therefore, not intended to indicate relative size, scale, and dimensions of the devices or components thereof, and/or to define or limit the scope of the exemplary implementations. Although specific terms are used in the following description for the sake of clarity, these terms are intended to refer only to the particular structure of the exemplary implementations selected for illustration in the drawings, and are not intended to define or limit the scope of the disclosure. In the drawings and the following description below, it is to be understood that like numeric designations refer to components of like function.

Figure 1A:
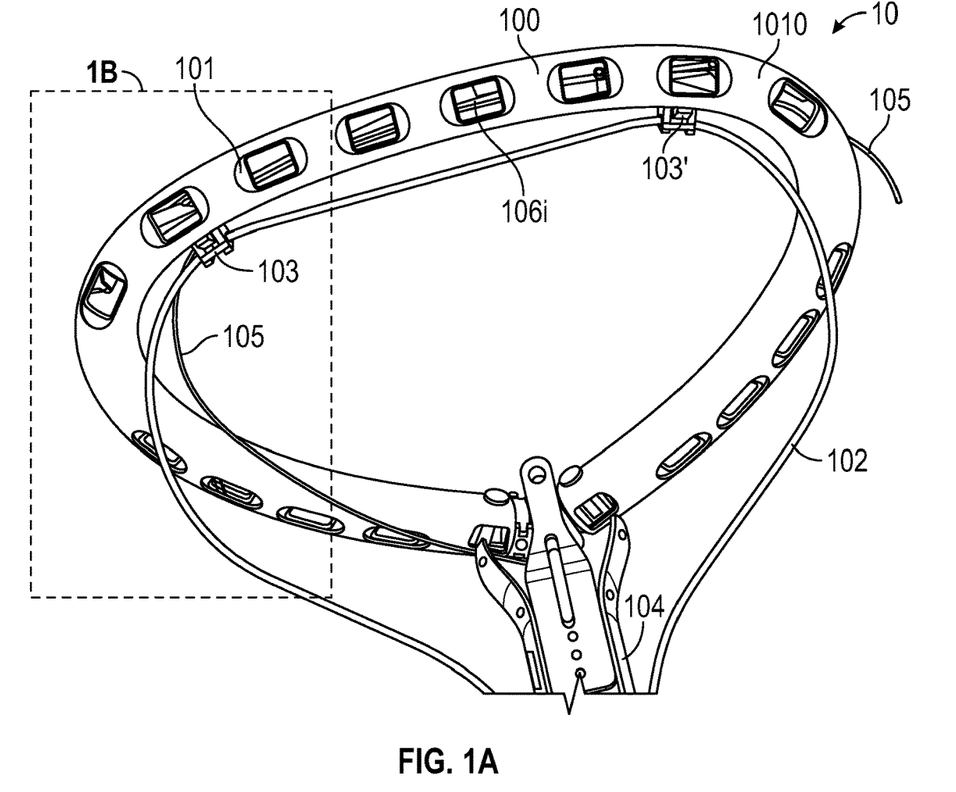
FIG. 1A illustrates a first exemplary implementation of the alignment member according to one embodiment of the present disclosure.
Figure 1B:
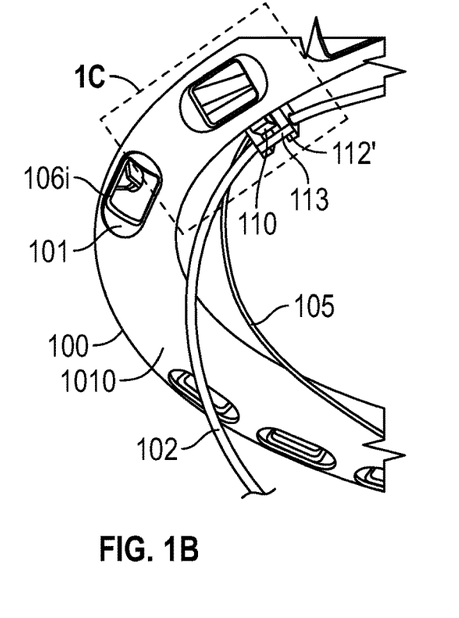
FIG. 1B illustrates an enlargement of the portion marked area in FIG. 1A.

Turning now to FIGS. 1A, 1B, illustrating an exemplary implementation of a method of aligning annuloplasty ring 100 with at least one natural fiducial (see, e.g., FIG. 4, 511, 512) in an annular target (see, e.g., FIG. 4, 501-504), implementable in system 10 comprising: annuloplasty ring 100 having an outer hollow tube 101, optionally covered by sleeve 1010, or toroidal portion thereof (not shown), with a plurality of segments formed by a slotted ribbon (not shown, see, e.g., commonly assigned U.S. application Ser. No. 16/702,338, filed Mar. 12, 2019 and titled "STABILIZING AND ADJUSTING TOOL FOR CONTROLLING A MINIMALLY INVASIVE MITRAL/TRICUSPID VALVE REPAIR SYSTEM", which is incorporated herein in its entirety, and referred to hereinafter as the "338 Application") operable to change outer hollow tube 101 from an insertion configuration to an operable configuration; alignment member 102, releasably coupled to outer hollow 101 tube via at least one coupling assembly 103, and at least one coupling assembly 103 configured to be aligned with the at least one natural fiducial (see, e.g., FIG. 4, 511, 512); and delivery catheter 104 (see, e.g., the '338 Application), adapted, sized, and configured to accommodate: alignment member 102 and annuloplasty ring 100 or its toroidal portion in its insertion configuration, wherein delivery catheter 104 is operable, once annuloplasty ring 100 or its toroidal portion is inserted, to alter outer hollow tube 101 from the insertion configuration to the operable configuration, the method comprising: using delivery catheter 104, introducing annuloplasty ring 100, or its toroidal portion, to annular target (see, e.g., FIG. 4, 501-504); using delivery catheter 104, altering the insertion configuration of annuloplasty ring 100 or its toroidal portion to the operable configuration; and using alignment member 102, aligning at least one coupling assembly 103 with at least one natural fiducial (see, e.g., FIG. 4, 511, 512), thereby aligning annuloplasty ring 100, or its toroidal portion with at least one natural fiducial (see, e.g., FIG. 4, 511, 512) in annular target (see, e.g., FIG. 4, 501-504), the method further comprises: anchoring annuloplasty ring 100 or its toroidal portion to a predetermined portion of annular target (see, e.g., FIG. 4, 501-504); and prior to, simultaneous with, or following the step of anchoring, releasing alignment member 102, from annuloplasty ring 100, or its toroidal portion.

Figure 1C:
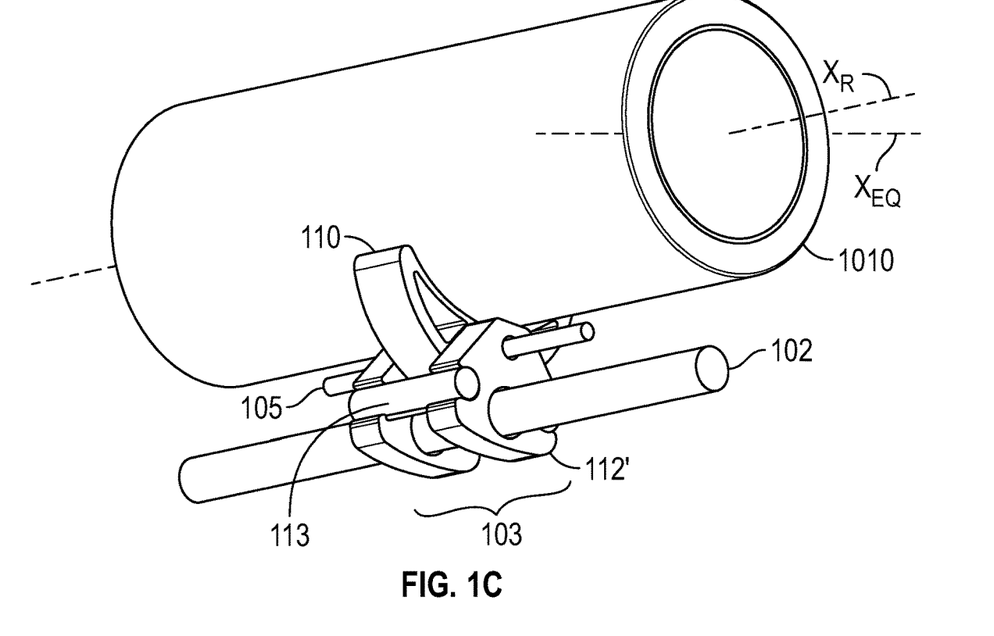
FIG. 1C illustrates an enlargement of the portion marked area in FIG. 1B.
Figure 1D:
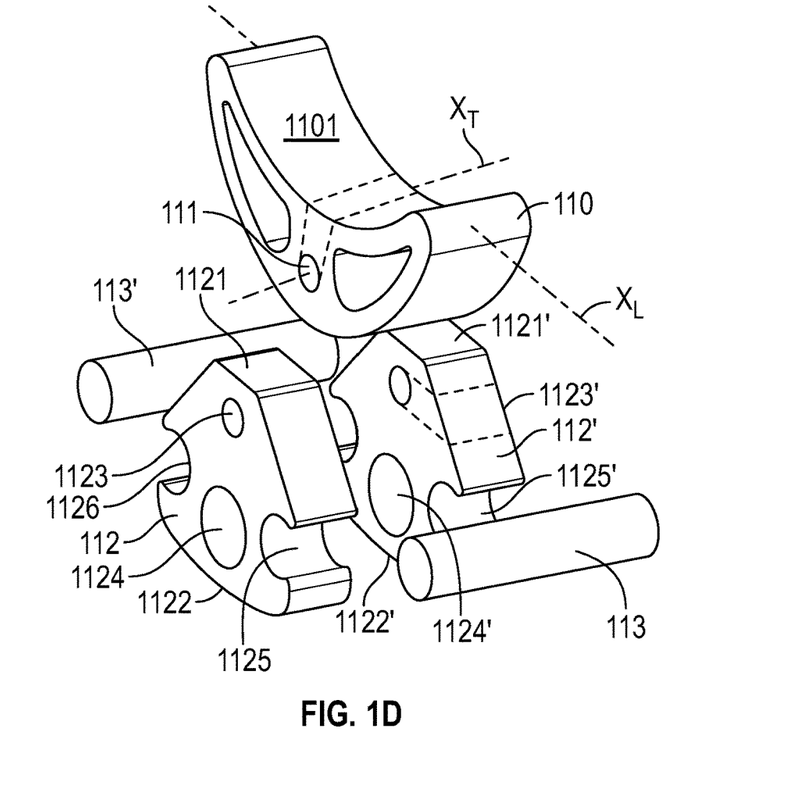
FIG. 1D illustrates an exploded view of the coupling assembly associated, for example, with the first exemplary implementation.

As further illustrated in FIGS. 1A-1D, in an exemplary implementation, alignment member 102 is a hairpin-shaped wire (refers generally to wire segment having two ends with an expanded U-shaped portion included between the two ends, e.g., a stem-loop structure, whether in the same or different plane as the two ends), releasably coupled to outer hollow tube 101 via at least two coupling assemblies 103, which can be coupled via sleeve 1010 covering hollow tube 101 either completely or partially. As illustrated, outer hollow tube 101 further defines a plurality of openings 106$i$, sized, adapted, and configured to allow a plurality of anchors (see, e.g., the '338 Application), to extend laterally, and engage the annulus of the annular target (see, e.g., FIG. 4, 501-504). Further, and as shown in FIGS. 1C and 1D, each of coupling assemblies 103, 103' comprise: fin 110 having arcuate apical surface 1101 defining longitudinal axis $X_L$, transversely coupled to outer hollow tube 101. In other words, longitudinal axis $X_L$ of fin 110, is substantially perpendicular to radial axis $X_R$ of hollow tube 101. While FIG. 1C illustrates fin 110 as being ventral to hollow tube 101, this is merely for illustration purposes as evident from FIGS. 1A and 1B. In certain exemplary implementations, the radial location of fin 110 relative to the plane defined by annuloplasty ring 100 will vary based on various parameters, such as, for example, the size of annuloplasty ring 100, the natural fiducial it is aligned with, the size and shape of the annular target, whether a complete annuloplasty ring or a toroidal portion thereof, and the like, may be between about 0 degrees and about 180 degrees off hollow tube's 101 equator (see, e.g., $X_{EQ}$, FIG. 1C) in a ventral direction.

As illustrated, fin 110 further defining bore 111 spanning fin 110 in a transverse direction $X_T$ to fin's 110 longitudinal axis $X_L$ configured to accommodate release cord 105 (see, e.g., FIGS. 1A-1C). Coupling assembly 103 further comprises a pair of plates 112, 112', each plate 112, 112' having apical end 1121, 1121' and basal end 1122, 1122', each with apical aperture 1123, 1123' defined toward apical end 1121, 1121' of plates 112, 112', apertures 1123, 1123' sized and configured to be aligned (in other words, coaxial) with bore 111 transversely $X_T$ spanning fin 110 and accommodate release cord 105, and basal aperture 1124, 1124' in each plate 112, 112' sized and configured to receive and accommodate a portion of alignment member 102, basal aperture 1124, 1124' defined toward basal end 1122, 1122' of plate 112, 112'. Plates 112' 112' further defining at least one recess 1125, 1125', sized and configured to engage bridging rod 113; and bridging rod 113, configured to couple first and second plate 112, 112' respectively, wherein fin 110 is sandwiched between pair of plates 112, 112', engaged via release cord 105 included in delivery catheter 104 that is configured to releasably couple pair of plates 112, 112' to fin 110 via basal aperture 1124, 1124'.

Accordingly, the step of releasing alignment member 102 in the method disclosed associated with the above-mentioned exemplary implementation comprises: using delivery catheter (see, e.g., the '338 Application); pulling release cord 105, thereby separating plates 112, 112' from fin 110; and retracting alignment member 102 into delivery catheter 104 (see, e.g., the '338 Application).

Figure 2A:
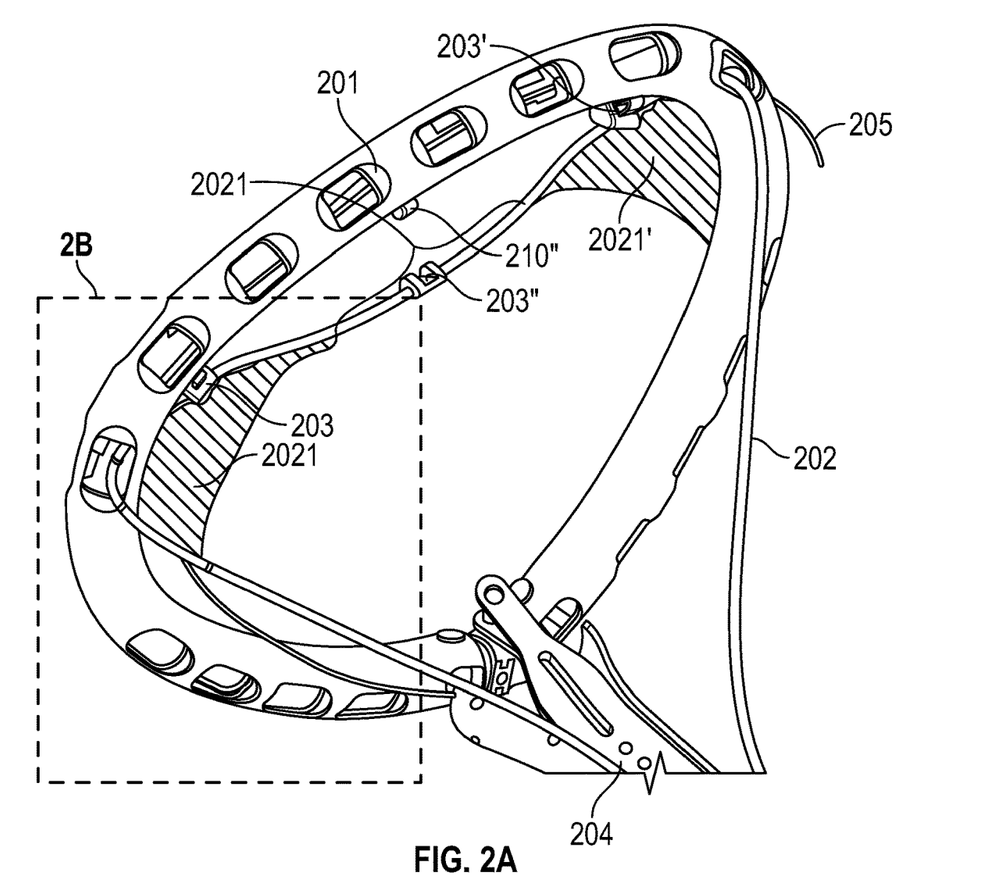
FIG. 2A illustrates a second exemplary implementation of the alignment member.

Turning now to FIGS. 2A-2D, illustrating another exemplary implementation. As illustrated in FIG. 2A, alignment member 202 is similar to hairpin-shaped wire alignment member 102, which further defines a pair of arcuate nodules 2021, 2021', releasably coupled to outer hollow tube 201 or sleeve 2010 via coupling assemblies 203, 203' (and optionally 203"), wherein a coupling assembly 203, 203' is coupled to alignment member 202 toward the center of each arcuate nodule 2021, 2021' and the step of aligning at least one of coupling assemblies 203, 203' (or, alternatively or additionally, coupling assembly 203") comprises aligning at least one of: coupling assemblies 203, 203' and 203", with at least one of the natural fiducials (see, e.g., FIG. 4, 511, 512, or the interleaflet triangle, the tricuspid posterior-anterior hinge, and a combination comprising one or more of the foregoing).

Figure 2B:
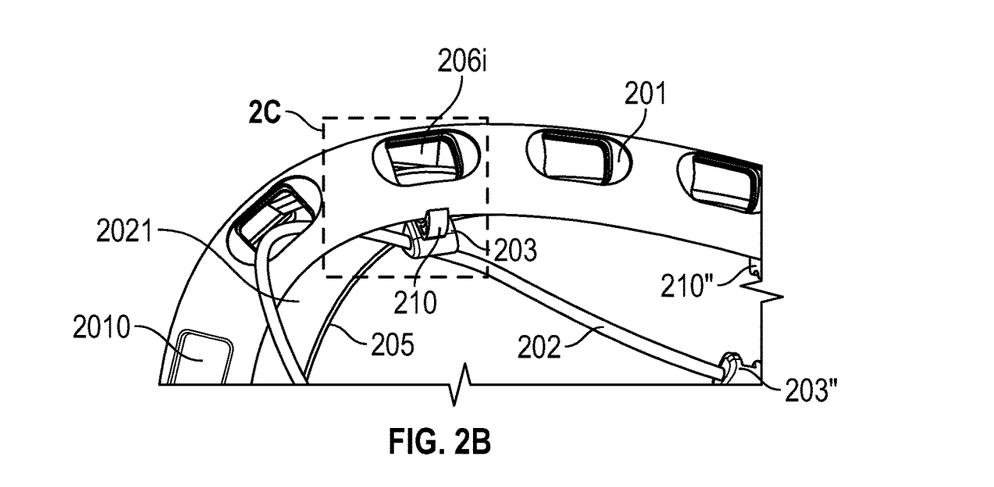
FIG. 2B illustrates an enlargement of the portion marked area in FIG. 2A.
Figure 2C:
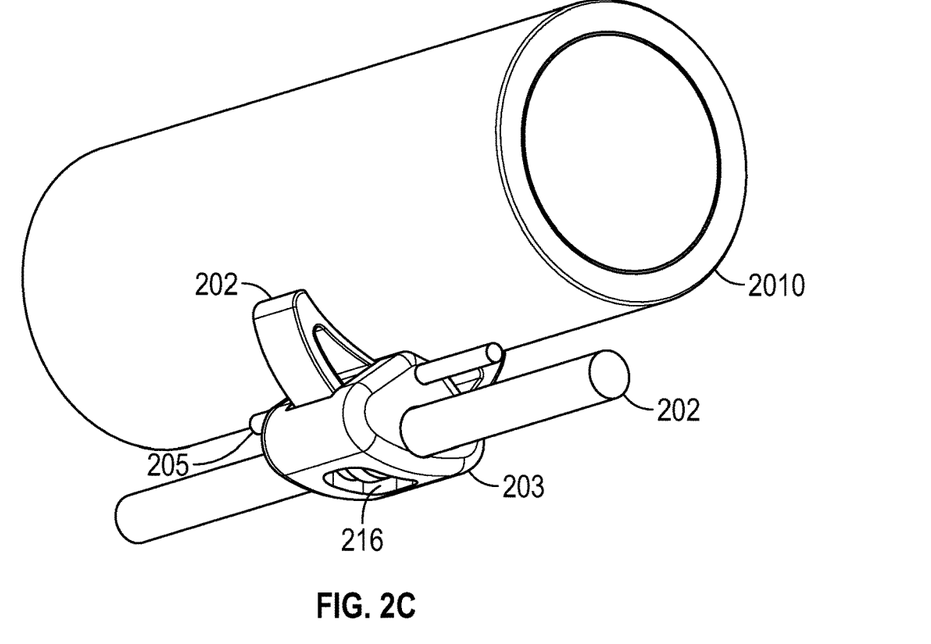
FIG. 2C illustrates an enlargement of the portion marked area in FIG. 2B.
Figure 2D:
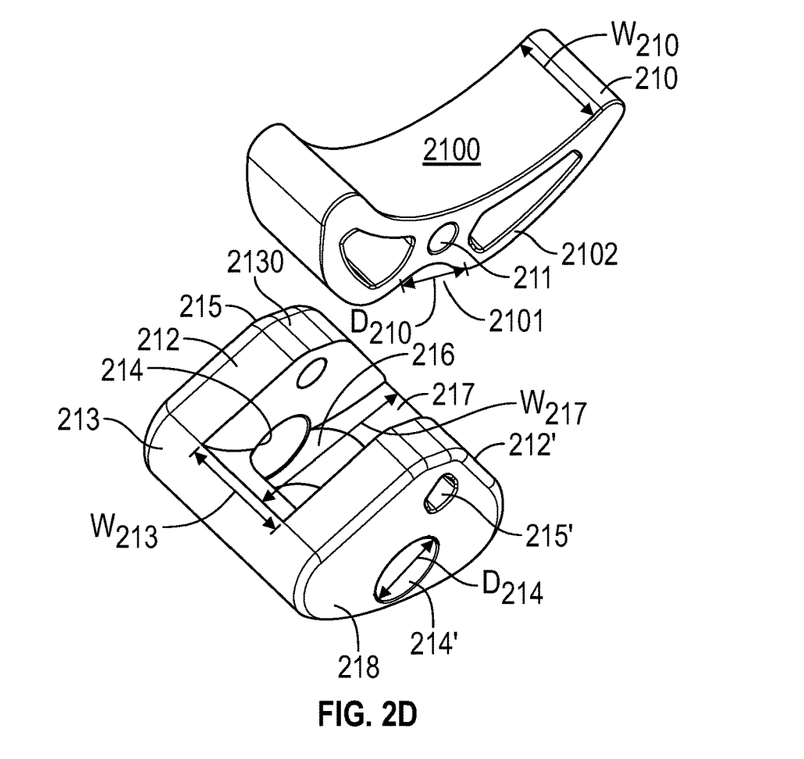
FIG. 2D illustrates an exploded view of the coupling assembly associated, for example, with the second exemplary implementation.

In addition, and as illustrated in FIGS. 2B-2D, each of the coupling assemblies 203, 203', or 203" comprise: fin 210 defining longitudinal axis $X_L$ (see, e.g., FIG. 1D), transversely coupled to outer hollow tube 201 or sleeve 2010, fin 210 further defining bore 211 spanning fin 210 in a transverse direction $X_T$ (see, e.g., FIG. 1D) to fin's 210 longitudinal axis $X_L$ (see, e.g., FIG. 1D). As illustrated in FIG. 2D, fin 210 comprises arcuate apical surface 2100, sized and configured to abut outer hollow tube 201 or sleeve 2010 over a substantial area thereof. Fin 210, having width $W_{210}$, further defines arcuate recess 2101 forming a semicylindrical structure having diameter $D_{210}$.

As illustrated in FIG. 2D, each coupling assembly 203, 203' or 203" further comprise: brace(s) 213, 213' 213" having apical end 2130 defining a pair of protrusions 212, 212' extending apically with gap 217 there-between, gap 217 having width $W_{217}$, sized and configured to accommodate the portion of fin 210 defining transverse bore 211, brace(s) 213, 213' 213" further having basal end 218, with apical aperture 215, 215' defined in each protrusion 212, 212' respectively, wherein each (apical) aperture 215, 215' is sized and configured to be aligned (in other words, form a coaxial hole) with bore 211 transversely spanning fin 210, as well as basal aperture 214, 214' (defined in each of protrusions 212, 212' respectively), brace(s) 213, 213' 213" sized and configured to receive and accommodate arcuate nodule portion 2021, 2021' (in braces 213, 213' or 2022 of brace 213" of alignment member 202 defined toward basal end 218 of brace(s) 213, 213' 213", wherein fin 210 is sandwiched between brace protrusions 212, 212', engaged via release cord 205 included in delivery catheter 204 and looped through each apical aperture 215, 215' configured to releasably couple the brace(s) 213, 213' 213" from fin 210, 210' (and optionally 210") via release cord(s) 205. As further illustrated in FIGS. 2C and 2D, when assembled, basal end 2102 of fin 210 having width $W_{210}$ is accommodated within gap 217, such that arcuate recess 2101 having diameter $D_{210}$, which is substantially similar to diameter $D_{214}$, is configured to form a coaxial covered tunnel with basal apertures 214, 214'. Also illustrated, is access opening 216 used in certain implementations to assemble coupling assembly 203.

Accordingly, and in an alternative implementation, the step of releasing, or decoupling coupling assembly(ies) 203, 203', and optionally 203", from alignment member 202 comprises: using delivery catheter 204 (see, e.g., the '338 Application); pulling release cord 205 thereby separating brace(s) 213, 213' 213" from fin(s) 210, 210', and optionally 210"; and retracting release cord 205 and alignment member 202 into delivery catheter 204 (see, e.g., the '338 Application).

Figure 3A:
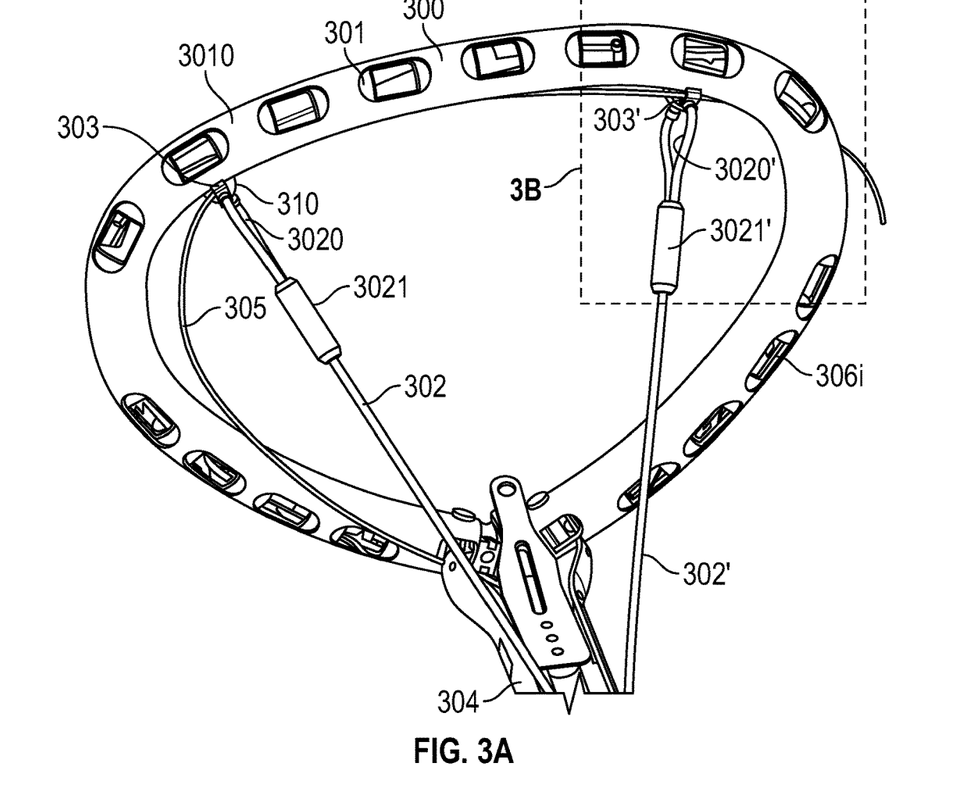
FIG. 3A illustrates a third exemplary implementation of the alignment member.

Turning now to FIGS. 3A-3D, illustrating yet another exemplary implementation of the systems used for implementing the methods disclosed herein. As illustrated in FIG. 3A, alignment member 302 comprises pair of stylets 302, 302', each stylet 302, 302' having distal eyelet 3020, 3020', releasably coupled to outer hollow tube 301 via at least one coupling assembly 303, 303', wherein coupling assembly 303, 303' is coupled to alignment member 302 through distal eyelet 3020, 3020'. Distal eyelet 3020, 3020' may be formed by looping the distal end of each stylet 302, 302' and clamping the end using, for example, clamp 3021, 3021'.

Figure 4:
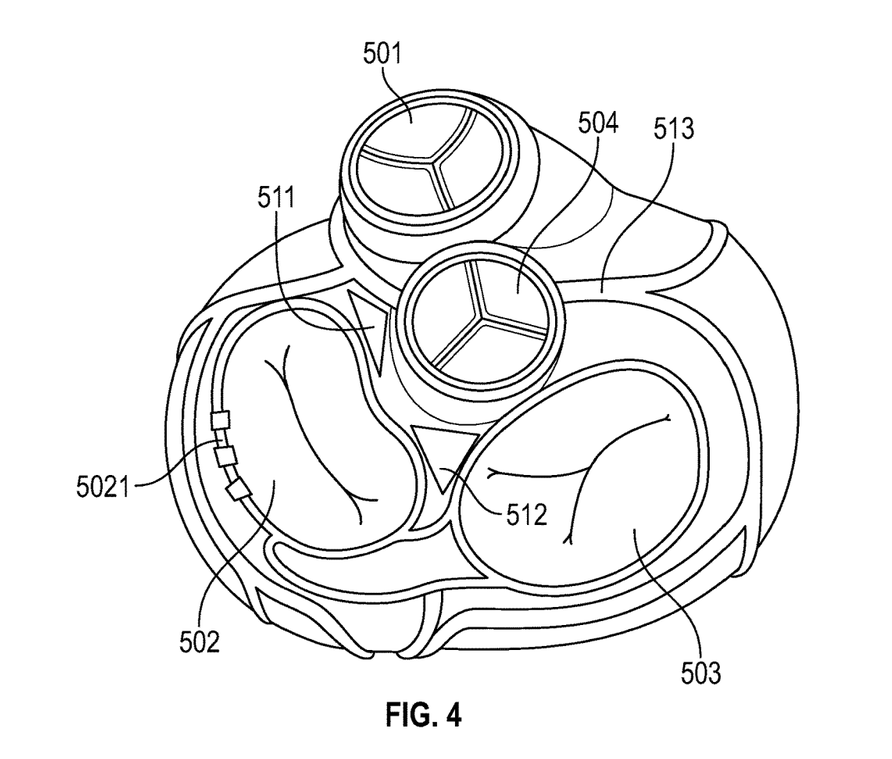
FIG. 4 is a schematic illustration of the heart valves including certain examples of natural fiducials.

Under this exemplary implementation, the step of aligning annuloplasty ring 300 or its toroidal portion with at least one natural fiducial (see, e.g., FIG. 4, 511, 512, or the interleaflet triangle, the tricuspid posterior-anterior hinge, and a combination comprising one or more of the foregoing), of an annular target (see, e.g., FIG. 4, 501-504), comprises aligning at least one of coupling assemblies 303, 303' with at least one of the natural fiducials (see, e.g., FIG. 4, 511, 512, or the interleaflet triangle, the tricuspid posterior-anterior hinge, and a combination comprising one or more of the foregoing).

Figure 3B:
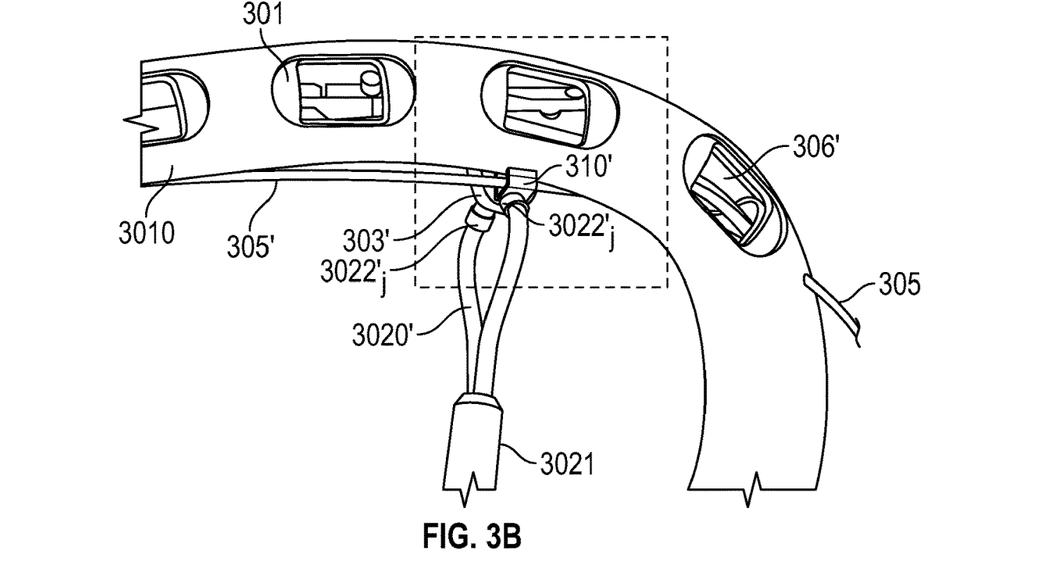
FIG. 3B illustrates an enlargement of the portion marked area in FIG. 3A.
Figure 3C:
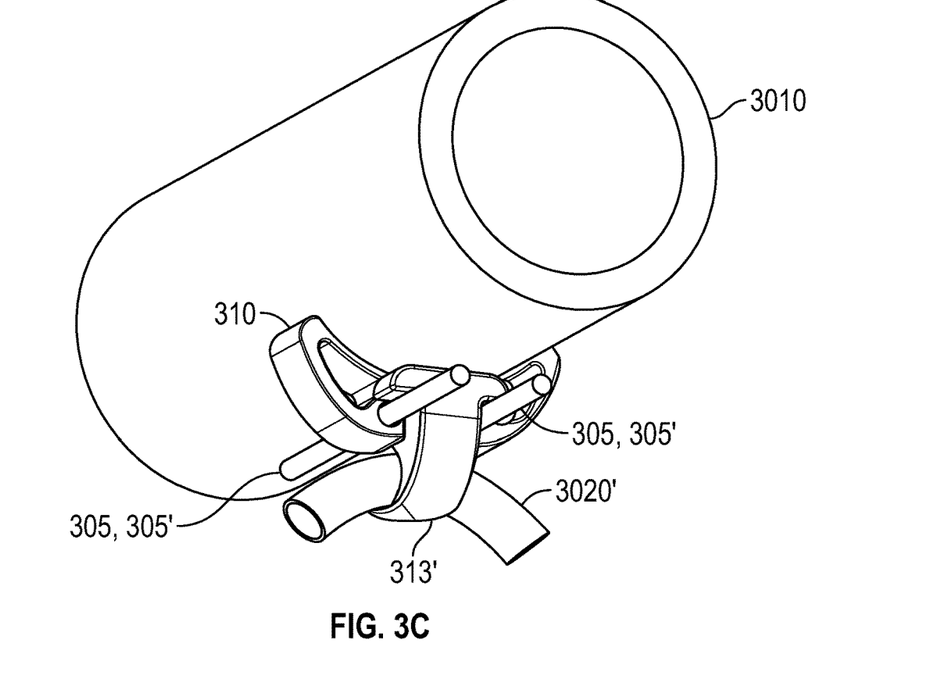
FIG. 3C illustrates an enlargement of the portion marked area in FIG. 3B.
Figure 3D:
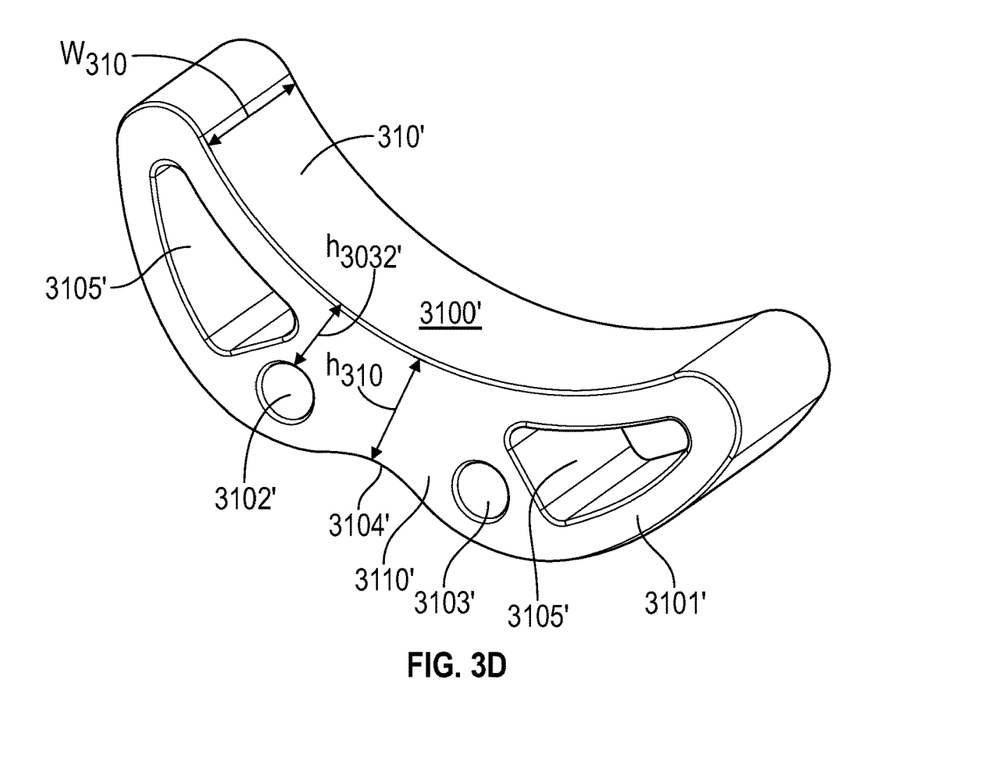
FIG. 3D illustrates an exploded view of the coupling assembly associated, for example, with the first exemplary implementation.

As illustrated in FIGS. 3B-3D, each coupling assembly 303, 303' comprises: fin 310' defining longitudinal axis $X_L$ (see, e.g., FIG. 1D), transversely coupled to outer hollow tube 301 or sleeve 3010, having arcuate apical surface 3100' (referring to a curved surface having a radial arc; the radius of curvature may vary, depending on the end use of the surface) abutting the hollow tube with a width $W_{310}$, and fin body 3110' extending basally from arcuate apical surface 3100, defining pair of drill holes 3102', 3103', each drill hole 3102', 3103' sized and configured to accommodate release cord 305, 305'.

Figure 3E:
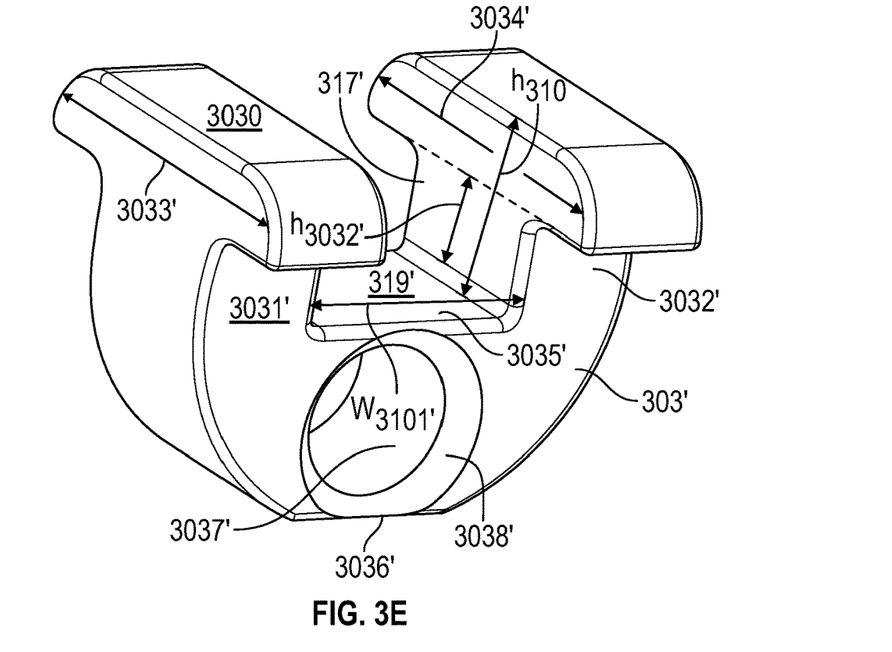
FIG. 3E illustrates a brace according to one embodiment of the present disclosure.

FIG. 3E also illustrates brace 313' (see, e.g., FIG. 3A), having apical end 3030 defining pair of flanged protrusions 3031', 3032' extending apically from floor 319', wherein flanges 3033', 3034' respectively extend laterally from each flanged protrusion 3031', 3032', with gap 317' between flanged protrusions 3031', 3032', gap 317 having width $W_{3101}$ sized and configured to accommodate width $W_{310}$, of fin body 3110', and basal end 3036' defining aperture 3037' in parallel with longitudinal axis $X_L$ of fin 310, wherein defining aperture 3037' having beveled rims 3038' sized and configured to receive and accommodate eyelet 3020, 3020' portion of each stylet 302, 302', and wherein fin 310 is at least partially sandwiched between pair of flanged protrusions 3031', 3032', engaged via pair of release cords 305, 305' looped through fin body 3110' included in delivery catheter 304, whereby each release cord 305, 305' looped through corresponding drill hole 3102', 3103' defined in fin body 3110', below laterally extending flange 3033', 3034' of flanged protrusions 3031', 3032' respectively, the pair of release cords 305, 305' configured to releasably couple the brace 313 to fin 310.

As illustrated, drill holes 3102', 3103' are defined in fin body 3110' at height $h_{310}$ from arcuate apical surface 3100' such that flanges 3033', 3034' rest atop release cords 305, 305' and the height $h_{310}$ of fin body 3110' from its basal end 3104' to arcuate apical surface 3100' is equal to the height $h_{310}$, from floor 319' to apical end 3030, thereby forming a single surface abutting outer hollow tube 301 or sleeve 3010.

Accordingly, and in an alternative implementation, the step of releasing, or decoupling coupling assembly(ies) comprises: using the delivery catheter (see, e.g., the '338 Application), pulling each of release cords 305, 305', thereby separating brace(s) 303, 303' from fin(s) 310, 310'; and again, using delivery catheter 304, retracting release cords 305, 305' and stylet(s) 302, 302' into delivery catheter 304 (see, e.g., the '338 Application).

In an exemplary implementation, annuloplasty ring 100, 200, 300 or its toroidal portion has one or more zones, each comprising a plurality of internal anchor members located at least partially within outer hollow tube 101, 201, 301 (see, e.g., the '338 Application), each anchor operable to selectably (in other words, on the user initiative without necessarily affecting other components or members) extend radially from outer hollow tube 101, 201, 301, for example through plurality of openings 106, 206, 306, and engage a portion of the annular target (see, e.g., FIG. 4, 501-504).

Accordingly, and in another exemplary implementation, following the step of introducing the annuloplasty ring, wherein annuloplasty ring 100, 200, 300 or its toroidal portion is elongated in the insertion configuration, and annular or arcuate (e.g., for the toroidal portion) in the operable configuration, in a trans-apical or trans-femoral approach (see, e.g., the '338 Application); the step of anchoring, annuloplasty ring 100, 200, 300 or its toroidal portion, comprises: deploying at least one of the plurality of anchors; and engaging the predetermined portion of the annular target (see, e.g., FIG. 4, 501-504), whereby the predetermined portion of the annular target, e.g., 502 engaged (see, e.g., FIG. 4, 501-504), can be, for example, the posterior portion 5021 of the annulus.

Accordingly and in an exemplary implementation, provided herein is a method of aligning an annuloplasty ring with at least one natural fiducial in an annular target, implementable in a system comprising: an annuloplasty ring having an outer hollow tube, or a toroidal portion thereof with a plurality of segments, operable to change the outer hollow tube from an insertion configuration to an operable configuration; an alignment member, releasably (meaning upon the application of reasonable manual force to the relevant members (e.g., the delivery catheter), the releasably coupled members will decouple) coupled to the outer hollow tube via at least one coupling assembly, the at least one coupling assembly configured to be aligned with the at least one natural fiducial; and a delivery catheter adapted, sized, and configured to accommodate: the alignment member and the annuloplasty ring in its insertion configuration, wherein the delivery catheter is operable, once the annuloplasty ring is inserted, to alter the outer hollow tube from the insertion configuration to the operable configuration, the method comprising: using the delivery catheter, introducing the annuloplasty ring or its toroidal portion to the annular target; using the delivery catheter, altering the insertion configuration of the annuloplasty ring or its toroidal portion to the operable configuration; and using the alignment member, aligning the at least one coupling assembly with the at least one natural fiducial, thereby aligning the annuloplasty ring or its toroidal portion with the at least one natural fiducial in the annular target, the method further (i) comprising: anchoring the annuloplasty ring or its toroidal portion to a predetermined portion of the annular target; and prior to, simultaneous with, or following the step of anchoring, releasing the alignment member, wherein (ii) the target is at least one of: a pulmonary valve, a mitral valve, a tricuspid valve, and an aortic valve, (iii) the at least one natural fiducial is the right fibrous trigon, the left fibrous trigon, the interleaflet triangle, the tricuspid posterior-anterior hinge, and a combination comprising one or more of the foregoing, (iv) the at least one annular target is the mitral valve or the tricuspid valve, wherein (v) the alignment member is a hairpin-shaped wire, releasably coupled to the outer hollow tube via at least two coupling assemblies, the alignment member comprises a pair of stylets, each stylet having a distal eyelet, releasably coupled to the outer hollow tube via at least one coupling assembly, wherein the coupling assembly is coupled to the alignment member in the eyelet, wherein (vi) the step of aligning comprises aligning at least one of the coupling assemblies with at least one of the natural fiducials, wherein (vii) each coupling assembly comprises: a fin defining longitudinal axis, transversely coupled to an outer hollow tube, having arcuate apical surface abutting the hollow tube, and fin body extending basally from the arcuate apical surface, defining a pair of drill holes, each drill hole sized and configured to accommodate a release cord; and a brace, having an apical end defining a pair of flanged protrusions extending apically, wherein the flanges extend laterally from each flanged protrusion, with a gap between the flanged protrusions, the gap having a width sized and configured to accommodate the width of a fin body, and a basal end defining an aperture in parallel with the longitudinal axis of the fin, sized and configured to receive and accommodate the eyelet portion of each stylet, and wherein the fin is sandwiched between the pair of flanged brace protrusions, engaged via the pair of release cords included in the delivery catheter and looped through the corresponding drill hole defined in the fin body, below the laterally extending flange of the flanged protrusions, the pair of release cords configured to releasably couple the brace to the fin, wherein (viii) the step of releasing comprises: pulling each of the release cords thereby separating the pair of flanged protrusions from the fin; and retracting the stylets into the delivery catheter, wherein (ix) the annuloplasty ring has one or more zones, each comprising a plurality of internal anchor members located at least partially within the outer hollow tube, each anchor operable to selectably extend radially from the outer hollow tube and engage a portion of the annular target, wherein (x) the step of anchoring comprises: deploying at least one of the plurality of anchors; and engaging the predetermined portion of the annular target, wherein (xi) the annular target is the mitral valve; the natural fiducial is at least one of: a right fibrous trigon and a left fibrous trigon; and the predetermined portion of the annular target engaged is the posterior portion of the annulus, wherein (xii) in the step of introducing, the annuloplasty ring is introduced in a trans-apical or trans-femoral approach, and (xiii) the annuloplasty ring or its toroidal portion is elongated in the insertion configuration, and annular in the operable configuration.

In another exemplary implementation, provided herein is a method of aligning an annuloplasty ring or a toroidal portion thereof with at least one natural fiducial in an annular target, implementable in a system comprising: an annuloplasty ring or a toroidal portion thereof, each having an outer hollow tube with a plurality of segments, operable to change the outer hollow tube from an insertion configuration to an operable configuration; an alignment member comprising a pair of stylets, each stylet having a distal eyelet, releasably coupled to the outer hollow tube via at least two coupling assemblies, wherein each coupling assembly is coupled to the alignment member via each eyelet and is configured to be aligned with the at least one natural fiducial; and a delivery catheter adapted, sized, and configured to accommodate: the alignment member and the annuloplasty ring or its toroidal portion in its insertion configuration, and wherein the delivery catheter is operable, once the annuloplasty ring is inserted, to alter the outer hollow tube from the insertion configuration to the operable configuration, the method comprising: using the delivery catheter, introducing the annuloplasty ring or its toroidal portion to the annular target; using the delivery catheter, altering the elongated insertion configuration of the annuloplasty ring to the operable annular configuration; and using the alignment members, aligning at least one of the pair of coupling assembly with the at least one natural fiducial, (xiv) the annular target is at least one of: a pulmonary valve, a mitral valve, a tricuspid valve, and an aortic valve, (xv) the at least one natural fiducial is at least one of: the right fibrous trigon, the left fibrous trigon, the interleaflet triangle, and the tricuspid posterior-anterior hinge, the method further (xvi) comprising: anchoring the annuloplasty ring or its toroidal portion to a predetermined portion of the annular target; and releasing the alignment member, wherein (xvii) each of the coupling assemblies comprises: a fin defining longitudinal axis, transversely coupled to an outer hollow tube, having arcuate apical surface abutting the hollow tube, and fin body extending basally from the arcuate apical surface, defining a pair of drill holes, each drill hole sized and configured to accommodate a release cord; and a brace, having apical end defining pair of flanged protrusions extending apically, wherein flanges extend laterally from each flanged protrusion, with gap between flanged protrusions, the gap having a width sized and configured to accommodate the width of the fin body, and a basal end defining an aperture in parallel with the longitudinal axis of the fin, sized and configured to receive and accommodate the eyelet portion of each stylet, and wherein the fin is sandwiched between the pair of flanged brace protrusions, engaged via the pair of release cords included in the delivery catheter and looped through the corresponding drill hole defined in the fin body, below the laterally extending flange of the flanged protrusions, the pair of release cords configured to releasably couple the brace to the fin, wherein (xviii) the step of releasing comprises: using the delivery catheter, pulling each of the release cords thereby separating the brace from the fin; and using the delivery catheter, retracting the release cords and the stylets into the delivery catheter, wherein (xix) the annuloplasty ring or its toroidal portion each has one or more zones, each zone comprising a plurality of internal anchor members located at least partially within the outer hollow tube, each anchor operable to selectably extend radially from the outer hollow tube and engage a portion of the annular target, the method (xx) further comprising: using the plurality of anchoring members, anchoring the annuloplasty ring or its toroidal portion to a predetermined portion of the annular target; and using the delivery catheter, releasing the alignment member from the annuloplasty ring or its toroidal portion, thereby aligning the annuloplasty ring with the at least one natural fiducial in the annular target, wherein (xxi) the step of anchoring comprises: deploying at least one of the plurality of anchors to engage the predetermined portion of the annular target; and engaging the predetermined portion of the annular target, wherein (xxii) wherein: the annular target is the tricuspid valve, or the mitral valve; the natural fiducial is at least one of: a right fibrous trigon, and a left fibrous trigon; the predetermined portion of the annular target engaged is the posterior rim of the annulus, wherein (xxiii) in the step of introducing, the annuloplasty ring or its toroidal portion is introduced in a trans-apical or trans-femoral approach, (xxiv) the annuloplasty ring or its toroidal portion is elongated in the insertion configuration, and annular in the operable configuration, wherein (xxv) the annuloplasty ring is comprised of at least one additional toroidal portion, operable, in combination with the toroidal portion, to form the annuloplasty ring, and wherein (xxvi) once formed, the annuloplasty ring has a saddle shape.

In yet another embodiment, provided herein is use of a system comprising: an annuloplasty ring or a toroidal portion thereof, each having an outer hollow tube with a plurality of segments, operable to change the outer hollow tube from an insertion configuration to an operable configuration; an alignment member comprising a pair of stylets, each stylet having a distal eyelet, releasably coupled to the outer hollow tube via at least two coupling assemblies, wherein each coupling assembly is coupled to the alignment member via each eyelet and is configured to be aligned with the at least one natural fiducial; and a delivery catheter adapted, sized, and configured to accommodate: the alignment member and the annuloplasty ring or its toroidal portion in its insertion configuration, and wherein the delivery catheter is operable, once the annuloplasty ring is inserted, to alter the outer hollow tube from the insertion configuration to the operable configuration, in the process of aligning an annuloplasty ring or a toroidal portion thereof with at least one natural fiducial in an annular target, by performing the steps of: using the delivery catheter, introducing the annuloplasty ring or its toroidal portion to the annular target; using the delivery catheter, altering the insertion configuration of the annuloplasty ring to the operable configuration; and using the alignment member, aligning the at least one coupling assembly with the at least one natural fiducial, thereby aligning the annuloplasty ring or its toroidal portion with the at least one natural fiducial in the annular target, wherein (xxvii) the annular target is at least one of: a pulmonary valve, a mitral valve, a tricuspid valve, and an aortic valve, (xxviii) the at least one natural fiducial is at least one of: the right fibrous trigon, the left fibrous trigon, the interleaflet triangle, and the tricuspid posterior-anterior hinge, the steps further (xxix) comprising: anchoring the annuloplasty ring or its toroidal portion to a predetermined portion of the annular target; and releasing the alignment member, wherein (xxx) each of the coupling assemblies comprises: a fin defining longitudinal axis, transversely coupled to an outer hollow tube, having an arcuate apical surface abutting the hollow tube, and a fin body extending basally from the arcuate apical surface, defining a pair of drill holes, each drill hole sized and configured to accommodate a release cord; and a brace, having an apical end defining a pair of flanged protrusions extending apically, wherein flanges extend laterally from each flanged protrusion, with a gap between flanged protrusions, the gap having a width sized and configured to accommodate the width of the fin body, and a basal end defining an aperture in parallel with the longitudinal axis of the fin, sized and configured to receive and accommodate the eyelet portion of each stylet, and wherein the fin is sandwiched between the pair of flanged brace protrusions, engaged via the pair of release cords included in the delivery catheter and looped through the corresponding drill hole defined in the fin body, below the laterally extending flange of the flanged protrusions, the pair of release cords configured to releasably couple the brace to the fin, wherein (xxxi) the step of releasing comprises: using the delivery catheter, pulling each of the release cords thereby separating the brace from the fin; and using the delivery catheter, retracting the release cords and the stylets into the delivery catheter, wherein (xxxii) the annuloplasty ring or its toroidal portion has one or more zones, each zone comprising a plurality of internal anchor members located at least partially within the outer hollow tube, each anchor operable to selectably extend radially from the outer hollow tube and engage a portion of the annular target, the steps (xxxiii) further comprising: using the plurality of anchoring members, anchoring the annuloplasty ring or its toroidal portion to a predetermined portion of the annular target; and using the delivery catheter, releasing the alignment member from the annuloplasty ring or its toroidal portion, thereby aligning the annuloplasty ring with the at least one natural fiducial in the annular target, wherein (xxxiv) the step of anchoring comprises: deploying at least one of the plurality of anchors to engage the predetermined portion of the annular target; and engaging the predetermined portion of the annular target, wherein (xxxv): the annular target is the tricuspid valve, or the mitral valve; the natural fiducial is at least one of: a right fibrous trigon and a left fibrous trigon; the predetermined portion of the annular target engaged is the posterior rim of the annulus, wherein (xxxvi) in the step of introducing, the annuloplasty ring or its toroidal portion is introduced in a trans-apical or trans-femoral approach, (xxxvii) the annuloplasty ring or its toroidal portion is elongated in the insertion configuration, and annular in the operable configuration, wherein (xxxviii) the annuloplasty ring is comprised of at least one additional toroidal portion, operable, in combination with the toroidal portion, to form the annuloplasty ring, and wherein (xxxix) once formed, the annuloplasty ring has a saddle shape.

While in the foregoing specification the methods, systems, subsystems, and kits for aligning an annuloplasty ring or a toroidal portion thereof with at least one natural fiducial in an annular target described herein have been described in relation to certain exemplary implementations, and many details are set forth for purpose of illustration, it will be apparent to those skilled in the art that the disclosure of the alignment methods, implementable using the systems disclosed herein, are susceptible to additional implementations and that certain of the details described in this specification and as are more fully delineated in the following claims can be varied considerably without departing from the basic principles disclosed herein.

What is claimed:

1. A method of aligning an annuloplasty ring with at least one natural fiducial in an annular target, implementable in a system comprising:
    an annuloplasty ring having an outer hollow tube, or a toroidal portion thereof with a plurality of segments, operable to change the outer hollow tube from an insertion configuration to an operable configuration;
    an alignment member, releasably coupled to the outer hollow tube via at least one coupling assembly, the at least one coupling assembly configured to be aligned with the at least one natural fiducial; and
    a delivery catheter adapted, sized, and configured to accommodate: the alignment member and the annuloplasty ring in the insertion configuration, wherein the delivery catheter is operable, once the annuloplasty ring is inserted, to alter the outer hollow tube from the insertion configuration to the operable configuration, the method comprising:
    using the delivery catheter, introducing the annuloplasty ring or the toroidal portion to the annular target;
    using the delivery catheter, altering the insertion configuration of the annuloplasty ring or the toroidal portion to the operable configuration; and
    using the alignment member, aligning the at least one coupling assembly with the at least one natural fiducial, thereby aligning the annuloplasty ring or the toroidal portion with the at least one natural fiducial in the annular target,
    wherein the at least one natural fiducial is a right fibrous trigon, a left fibrous trigon, a interleaflet triangle, a tricuspid posterior-anterior hinge, or a combination comprising one or more of the foregoing,
    wherein the alignment member comprises a pair of stylets, each stylet having a distal eyelet, releasably coupled to the outer hollow tube via the at least one coupling assembly, wherein the at least coupling assembly is coupled to the alignment member in the distal eyelet,
    wherein using the aligning member comprises aligning at least one of the coupling assemblies with at least one of the at least one natural fiducials, wherein each coupling assembly comprises:
a fin defining a longitudinal axis, transversely coupled to the outer hollow tube, having an arcuate apical surface abutting the outer hollow tube, and a fin body extending basally from the arcuate apical surface, defining a pair of drill holes, each drill hole sized and configured to accommodate a release cord; and
a brace, having an apical end defining a pair of flanged protrusions extending apically, wherein the flanges extend laterally from each flanged protrusion, with a gap between the flanged protrusions, the gap having a width sized and configured to accommodate a width of the fin body, and a basal end defining an aperture in parallel with the longitudinal axis of the fin, sized and configured to receive and accommodate the distal eyelet portion of each stylet, and
wherein the fin is sandwiched between the pair of flanged protrusions, engaged via a pair of release cords included in the delivery catheter and looped through a corresponding drill hole of the pair of drill holes defined in the fin body, below the laterally extending flange of the flanged protrusions, the pair of release cords configured to releasably couple the brace to the fin.

2. The method of claim 1, further comprising:
anchoring the annuloplasty ring or the toroidal portion to a predetermined portion of the annular target; and
prior to, simultaneous with, or following the step of anchoring, releasing the alignment member.

3. The method of claim 1, wherein the target is at least one of: a pulmonary valve, a mitral valve, a tricuspid valve, and an aortic valve.

4. The method of claim 2, wherein the step of releasing comprises:
pulling each one of the pair of release cords thereby separating the pair of flanged protrusions from the fin; and
retracting the stylets into the delivery catheter.

5. The method of claim 2, wherein the annuloplasty ring has one or more zones, each comprising a plurality of anchors located at least partially within the outer hollow tube, each anchor operable to selectably extend radially from the outer hollow tube and engage a portion of the annular target.

6. The method of claim 5, wherein the step of anchoring comprises:
deploying at least one of the plurality of anchors; and
engaging the predetermined portion of the annular target.

7. The method of claim 6, wherein:
the annular target is a mitral valve;
the at least one natural fiducial is at least one of: the right fibrous trigon and the left fibrous trigon; and
the predetermined portion of the annular target engaged is a posterior portion of an annulus.

8. The method of claim 1, wherein, in the step of introducing, the annuloplasty ring is introduced in a trans-apical or trans-femoral approach.

9. The method of claim 1, wherein the annuloplasty ring or the toroidal portion is elongated in the insertion configuration, and annular in the operable configuration.

10. A method of aligning an annuloplasty ring, or a toroidal portion thereof with at least one natural fiducial in an annular target, implementable in a system comprising:
an annuloplasty ring or a toroidal portion thereof, having an outer hollow tube with a plurality of segments, operable to change the outer hollow tube from an insertion configuration to an operable configuration;
an alignment member comprising a pair of stylets, each stylet having a distal eyelet, releasably coupled to the outer hollow tube via at least two coupling assemblies, wherein each coupling assembly of the two coupling assemblies is coupled to the alignment member via each distal eyelet and is configured to be aligned with the at least one natural fiducial; and
a delivery catheter adapted, sized, and configured to accommodate: the alignment member and the annuloplasty ring or its toroidal portion in its insertion configuration, and wherein the delivery catheter is operable, once the annuloplasty ring is inserted, to alter the outer hollow tube from the insertion configuration to the operable configuration, the method comprising:
using the delivery catheter, introducing the annuloplasty ring or its toroidal portion to the annular target;
using the delivery catheter, altering the insertion configuration of the annuloplasty ring to the operable annular configuration;
using the alignment member, aligning the at least one of the two coupling assemblies with the at least one natural fiducial;
wherein each of the two coupling assemblies comprises:
a fin defining a longitudinal axis, transversely coupled to the outer hollow tube, having an arcuate apical surface abutting the outer hollow tube, and a fin body extending basally from the arcuate apical surface, defining a pair of drill holes, each drill hole sized and configured to accommodate a release cord; and
a brace, having an apical end defining a pair of flanged protrusions extending apically, wherein the flanges extend laterally from each flanged protrusion, with a gap between the pair of flanged protrusions, the gap having a width sized and configured to accommodate a width of the fin body, and a basal end defining an aperture in parallel with the longitudinal axis of the fin, sized and configured to receive and accommodate the distal eyelet of each stylet, and
wherein the fin is sandwiched between the pair of flanged brace protrusions, engaged via a pair of release cords included in the delivery catheter and looped through a corresponding drill hole of the pair of drill holes defined in the fin body, below the laterally extending flange of the flanged protrusions, the pair of release cords configured to releasably couple the brace to the fin.

11. The method of claim 10, wherein the annular target is at least one of: a pulmonary valve, a mitral valve, a tricuspid valve, and an aortic valve.

12. The method of claim 10, wherein the at least one natural fiducial is one of: a right fibrous trigon, a left fibrous trigon, a interleaflet triangle, and a tricuspid posterior-anterior hinge.

13. The method of claim 10, further comprising:
anchoring the annuloplasty ring or the toroidal portion to a predetermined portion of the annular target; and
releasing the alignment member.

14. The method of claim 13, wherein the step of releasing comprises:
using the delivery catheter, pulling each one of the pair of release cords thereby separating the brace from the fin; and
using the delivery catheter, retracting the pair of release cords and the stylets into the delivery catheter.

15. The method of claim 10, wherein the annuloplasty ring or the toroidal portion each has one or more zones, each zone comprising a plurality of anchors located at least partially within the outer hollow tube, each anchor operable to selectably extend radially from the outer hollow tube and engage a portion of the annular target.

16. The method of claim 15, further comprising:
using the plurality of anchoring members, anchoring the annuloplasty ring or the toroidal portion to a predetermined portion of the annular target; and
using the delivery catheter, releasing the alignment member from the annuloplasty ring or the toroidal portion, thereby aligning the annuloplasty ring with the at least one natural fiducial in the annular target.

17. The method of claim 16, wherein the step of anchoring comprises:
deploying at least one of the plurality of anchors to engage the predetermined portion of the annular target; and
engaging the predetermined portion of the annular target.

18. The method of claim 17, wherein:
the annular target is a tricuspid valve or a mitral valve;
the at least one natural fiducial is at least one of: a right fibrous trigon and a left fibrous trigon; and
the predetermined portion of the annular target engaged is a posterior rim of an annulus.

19. The method of claim 10, wherein, in the step of introducing, the annuloplasty ring or the toroidal portion is introduced in a trans-apical or trans-femoral approach.

20. The method of claim 10, wherein the annuloplasty ring or the toroidal portion is elongated in the insertion configuration, and annular in the operable configuration.

21. The method of claim 10, comprising at least one additional toroidal portion, operable, in combination with the toroidal portion, to form the annuloplasty ring.

22. The method of claim 21, wherein once formed, the annuloplasty ring has a saddle shape.

* * * * *